US005629013A

United States Patent [19]

Upson et al.

[11] Patent Number: 5,629,013
[45] Date of Patent: *May 13, 1997

[54] CHEWABLE CALCIUM CARBONATE ANTACID TABLET COMPOSITIONS

[75] Inventors: James G. Upson, Springdale; Carmelita M. Russell, Cincinnati, both of Ohio

[73] Assignee: The Procter & Gamble Company, Cincinnati, Ohio

[*] Notice: The term of this patent shall not extend beyond the expiration date of Pat. No. 5,244,670.

[21] Appl. No.: 234,510

[22] Filed: Apr. 28, 1994

Related U.S. Application Data

[63] Continuation of Ser. No. 104,282, Aug. 11, 1993, abandoned, which is a continuation of Ser. No. 874,663, Apr. 27, 1992, abandoned, which is a continuation-in-part of Ser. No. 680,459, Apr. 4, 1991, abandoned.

[51] Int. Cl.$^6$ .................................................. A61K 9/28
[52] U.S. Cl. .......................... 424/441; 424/439; 424/440; 424/687; 424/715; 424/464; 514/819
[58] Field of Search ........................ 424/439, 440, 424/441, 687, 464, 715; 514/819

[56] References Cited

U.S. PATENT DOCUMENTS

| | | | |
|---|---|---|---|
| 3,492,131 | 1/1970 | Schlatter | 99/141 |
| 3,991,178 | 11/1976 | Humbert et al. | 424/54 |
| 4,136,163 | 1/1979 | Watson et al. | 424/54 |
| 4,163,777 | 8/1979 | Mitra | 424/468 |
| 4,238,475 | 12/1980 | Witzel et al. | 424/48 |
| 4,446,135 | 5/1984 | Fountaine | 424/154 |
| 4,459,425 | 7/1984 | Amano et al. | 568/670 |
| 4,486,412 | 12/1984 | Shah et al. | 424/456 |
| 4,533,543 | 8/1985 | Morris et al. | 424/38 |
| 4,684,534 | 8/1987 | Valentine | 427/3 |
| 4,783,331 | 11/1988 | Alexander et al. | 424/44 |
| 4,800,095 | 1/1989 | Carroll et al. | 426/548 |
| 4,865,847 | 9/1989 | Gosswein | 424/439 |
| 4,882,152 | 11/1989 | Yang et al. | 424/440 |
| 4,882,154 | 11/1989 | Yang et al. | 424/440 |
| 4,942,039 | 7/1990 | Duvall et al. | 424/466 |
| 4,952,402 | 8/1990 | Sparks et al. | 424/419 |
| 4,975,270 | 12/1990 | Kehoe | 424/48 |
| 5,057,319 | 10/1991 | Gottwald et al. | 424/441 |
| 5,068,109 | 11/1991 | Foldager et al. | 424/441 |
| 5,102,665 | 4/1992 | Schaeffer | 424/466 |

FOREIGN PATENT DOCUMENTS

| 310299 | 4/1989 | European Pat. Off. | A61K 7/48 |
|---|---|---|---|

OTHER PUBLICATIONS

Chemical Abstracts, vol. 111, No. 18, Item No. 160226s, Issued 1988.
Chemical Abstracts, vol. 80, No. 16, Item No. 87516w, Issued 1974.
Jabloner et al., "A Molecular Approach to Flavor Synthesis, Menthol Esters of Varying Size and Polarity", J. Polym. Sci., Polym. Chem. Ed., 18(10), pp. 2933–2940 (1980).
Chemical Abstract Service, Abstract No. 88:11744p.
Chemical Abstract Service, Abstract No. 103(2):11234a.
Chemical Abstract Service, Abstract No. 107(8):64668j.
Chemical Abstract Service, Abstract No. 108(2):11014g.
Chemical Abstract Service, Abstract No. 110(16):141301a.
Chemical Abstract Service, Abstract No. 110(18):160412d.
Physicians' Desk Reference For Nonprescription Drugs, 13th Edition (Medical Economics Company Inc.; 1992); "Maalox" products at pp. 649–651; Tums products at pp. 720–721; and Rolaids products at pp. 757–758.
Gennaro, Remington's Pharmaceutical Science, 17th Edition (Mack Publishing Company; 1985), pp. 792–793.

*Primary Examiner*—Raj Bawa
*Attorney, Agent, or Firm*—Kim William Zerby; Douglas C. Mohl; Jacobus C. Rasser

[57] ABSTRACT

Chewable antacid tablet compositions comprising calcium carbonate sweetened with aspartame, and preferably also saccharin wherein said composition is in a solid unit dose form to be ingested by chewing.

5 Claims, No Drawings

CHEWABLE CALCIUM CARBONATE ANTACID TABLET COMPOSITIONS

This is a continuation of application U.S. Ser. No. 08/104,282, filed on Aug. 11, 1993, now abandoned, which is a continuation of application U.S. Ser. No. 07/874,663, filed on Apr. 27, 1992, now abandoned, which is a continuation-in-part application of U.S. Ser. No. 680,459, filed on Apr. 4, 1991, now abandoned.

BACKGROUND OF THE INVENTION

The present invention relates to chewable antacid tablet compositions sweetened with aspartame, and preferably sweetened with aspartame and saccharin.

Pharmaceutical compositions, such as antacids, useful for treating upper gastrointestinal tract distress (such as heartburn, indigestion, stomachache, etc.) are widely used. They vary depending on the active ingredients, and increasingly differ in the flavors, texture and even forms. The excipients for such compositions are chosen not only as appropriate for the dose form, but also to provide the best possible aesthetics for the compositions, including texture, flavor, after-taste, etc. A common antacid active ingredient is calcium carbonate.

In spite of the large amount of research directed to providing aesthetically-acceptable antacid tablet compositions containing calcium carbonate for treating upper gastrointestinal distress, there continues to be a need for compositions which have further improvements in aesthetics. Surprisingly, it has been discovered that including the sweetener aspartame (preferably in combination with saccharin) provides chewable calcium carbonate antacid tablets having improved aesthetics.

Thus, it is an object of the present invention to provide chewable calcium carbonate-containing antacid tablet compositions containing a level of calcium carbonate active useful for treating upper gastrointestinal tract distress (e.g., upset stomach, heartburn, indigestion) and sweetened with aspartame which are recognized as having improved aesthetics. Furthermore, an object is to provide methods for treating upper gastrointestinal distress by administering the chewable tablet compositions according to the present invention.

These and other objects of the present invention will become readily apparent from the detailed description which follows.

All percentages and ratios used herein are by weight, and all measurements are made at 25° C., unless otherwise specified.

SUMMARY OF THE INVENTION

The present invention is directed to a chewable calcium carbon- ate-containing antacid tablet composition comprising: (a) a safe and antacid effective amount of calcium carbonate useful for treating upper jastrointestinal tract distress; (b) from about 0.05% to about 1% aspartame, and, optionally, (c) from 0% to about 1% saccharin; and wherein further said composition is in a unit dose form to be totally ingested by chewing.

The present invention is also directed to methods for treating upper gastrointestinal tract distress. These methods comprise orally administering, by chewing, to a human patient in need of such treatment a safe and antacid effective amount of a chewable tablet composition according to the present invention.

DETAILED DESCRIPTION OF THE INVENTION

The present invention relates to pharmaceutical compositions comprising: (a) a safe and antacid effective amount of calcium carbonate useful for treating upper gastrointestinal tract distress; (b) from about 0.05% to about 1% aspartame; and, preferably, (c) from about 0.01% to about 1% saccharin.

The chewable tablet compositions of the present invention therefore comprise a safe and antacid effective amount of calcium carbonate useful for treating upper gastrointestinal tract distress. Typically the calcium carbonate comprises from about 1% to about 99%, by weight, of the tablet compositions of the present invention, preferably from about 10% to about 60%, and most preferably from about 30% to about 50%.

The chewable tablet compositions also comprise from about 0.05% to about 1%, preferably from about 0.1% to about 0.5%, and most preferably from about 0.1% to 0.3%, of aspartame. Aspartame is commercially available as Equal® and NutraSweet® (sold by the NutraSweet Company), and is more fully described in The Merck Index, 10th Edition, No. 852, "Aspartame" (Merck & Co., Inc.; 1983), and in U.S. Pat. No. 3,492,131, to Schlatter, issued Jan. 27, 1970, the disclosures of which are incorporated herein by reference in their entirety.

A preferred optional component for use in the chewable tablet compositions is saccharin, especially the sodium salt thereof, which also is a commercially available nonnutritive sweetener. This preferred optional component is more fully described in The Merck Index, 10th Edition, No. 8170, "Saccharin", and No. 8171, "Saccharin Soluble" (Merck & Co., Inc.; 1983), the disclosures of which are incorporated herein by reference in their entirety. The chewable cablet compositions preferably comprise saccharin in amounts from about 0.01% to about 1%, more preferably from about 0.01% to about 0.5%, and most preferably from about 0.05% to about 0.2%.

The pharmaceutical compositions of the present invention also preferably comprise an amount of 3-1-menthoxy propane 1,2-diol ("MPD") effective for providing a cooling sensation to the throat. This material is described in detail in U.S. Pat. No 4,459,425, issued Jul. 10, 1984 to Amano et al., incorporated herein by reference in its entirety. MPD is commercially available, being sold by Takasago Perfumery Co., Ltd., Tokyo, Japan. The MPD typically comprises from about 0.01% to about 0.50% by weight of the pharmaceutical compositions of the present invention, preferably from about 0.02% to about 0.20%, and most preferably from about 0.04% to about 0.10%.

In addition, excipients other than saccharin and/or the MPD may optionally be included in the present compositions. The term "excipients", as used herein, means one or more compatible solid or liquid filler diluents or encapsulating substances which are suitable for oral administration to a human by chewing such that the entire chewable tablet composition of the present invention is ingested. The term "compatible", as used herein, means that the components of the compositions of the present invention are capable of being commingled with the calcium carbonate and aspartame, and with each other, in a manner such that there is no interaction which would substantially reduce the antacid efficacy of the compositions under ordinary use situations, and therefore should not substantially interfere with the stomach acid neutralizing effect of the calcium carbonate. Preferably, the stomach acid neutralizing capacity of the calcium carbonate delivered to the stomach by the present invention tablets is greater than the stomach acid neutralizing capacity of about 100 mg of 100% calcium carbonate. Excipients must, of course, be of sufficiently high purity and sufficiently low toxicity to render them suitable for ingestion by the human being treated.

Some examples of substances which can serve as excipients in addition to the MPD and saccharin are sugars such as lactose, glucose and sucrose; starches such as corn-starch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame, oil, olive oil, corn oil and oil of theobroma; polyols such as propylene glycol, glycerine, sorbitol, mannitol, and polyethylene glycol; agar; and alginic acid; as well as other non-toxic compatible substances used in chewable tablet formulations. Wetting agents and lubricants such as sodium lauryl sulfate, as well as coloring agents, flavoring agents, sweetening agents (including other nonnutritive sweeteners), tableting agents, stabilizers, antioxidants, cooling agents, and preservatives, can also be present. Other compatible pharmaceutical additives and actives (e.g., other pharmaceutical actives useful for treating upper gastrointestinal tract distress; NSAI drugs; pain killers; muscle relaxants) may be included in the compositions of the present invention. Also, it is to be noted that in addition to the MPD, other materials having cooling properties may optionally be included within the excipients, such as menthol, menthol-like compounds such as N-ethyl-p-menthane-3-carboxamide ("WS-3", supplied by Sterling Drugs), and mixtures thereof. Preferred compositions comprise WS-3 at a level of from about 0.01% to about 0.5%, and more preferably from about 0.01% to about 0.1%.

Excipients suitable for the preparation of chewable tablets are well-known in the art. Their selection will depend on secondary considerations like taste, cost, shelf stability, which are not critical for the purposes of the present invention, and can be made without difficulty by a person skilled in the art.

The excipients employed in the present chewable tablet compositions are used at concentrations sufficient to provide a practical size to dosage relationship. Typically, excipients comprise from about 1% to about 99% by weight of the pharmaceutical compositions of the present invention, preferably from about 40% to about 90%, and most preferably from about 50% to about 70%.

The present invention also relates to methods for treating upper gastrointestinal tract distress in humans. These methods comprise orally administering, by chewing, to a human in need of such treatment a safe and antacid effective amount of a chewable tablet composition of the present invention.

The following examples further describe and demonstrate embodiments within the scope of the present invention. These examples are given solely for the purpose of illustration and are not to be construed as a limitation of the present invention as many variations thereof are possible without departing from the spirit and scope.

EXAMPLE I

An ingestible pharmaceutical composition according to the present invention in the form of a chewable antacid tablet is prepared as follows:

| Ingredients | Weight % |
| --- | --- |
| Granulated calcium carbonate[1] | 42.87% |
| Magnesium stearate | 2.50% |
| Colored speckles | 0.75% |
| Flavorants | 0.78% |
| MPD[2] | 0.07% |
| WS-3[3] | 0.05% |
| Aspartame | 0.198% |
| Sodium Saccharin | 0.102% |
| Mannitol[4] | Q.S. |

[1] Granulated calcium carbonate containing 93.3% calcium carbonate, 6.3% glucose and 0.4% gelatin; supplied by Whittaker Clark & Daniels, Philadelphia, Pa.
[2] 3-1-menthoxy propane 1,2-diol, supplied by Takasago Perfumery Co., Ltd., Tokyo, Japan.
[3] N-ethyl-p-menthane-3-carboxamide, supplied by Sterling Drugs.
[4] Granulate mannitol supplied by ICI Americas, Inc., Wilmington, Delaware.

The above ingredients are dry blended in a mixer until homogeneous, and then direct compressed in a tabletting machine to approximately 8.5 Strong Cobb units hardness to produce chewable antacid tablets each weighing 1.25 g (500 mg calcium carbonate per tablet). These tablets may also be prepared by utilizing granulated calcium carbonate which is a 50/50 coblend of calcium carbonate/mannitol.

Ingestion by chewing of one or two of these tablets by a human subject suffering from heartburn, acid( indigestion and upset stomach associated with these symptoms provides effective relief for this upper gastrointestinal tract distress.

What is claimed is:

1. A chewable calcium carbonate-containing antacid tablet composition consisting essentially of:
    (a) from about 1% to about 99% of calcium carbonate useful for treating upper gastrointestinal tract distress;
    (b) from about 0.05% to about 1% of aspartame;
    (c) from about 0.01% to about 1% of saccharin; and
    (d) from about 1% to about 99% of at least one excipient comprising 3-1-methoxypropane 1,2-diol;
    and wherein further said composition is in a solid unit dose form to be ingested by chewing.

2. A chewable calcium carbonate-containing antacid tablet composition consisting essentially of:
    (a) from about 10% to about 60% of calcium carbonate;
    (b) from about 0.05% to about 1% of aspartame;
    (c) from about 0.01% to about 0.5% of saccharin; and
    (d) from about 40% to about 90% of at least one excipient comprising 3-1-menthoxy propane 1,2-diol;
    and wherein further said composition is in a solid unit dose form to be ingested by chewing.

3. A chewable calcium carbonate-containing antacid tablet composition according to claim 2 comprising from about 0.01% to about 0.50% of 3-1-menthoxy propane 1,2-diol.

4. A chewable calcium carbonate-containing antacid tablet composition consisting essentially of:
    (a) from about 30% to about of 50% calcium carbonate;
    (b) from about 0.1% to about 0.3% of aspartame;
    (c) from about 0.05% to about 0.2% of sodium saccharin; and
    (d) from about 50% to about 70% of at least one excipient comprising 3-1-menthoxy propane 1,2-diol;
    and wherein further said composition is in a solid unit dose form to be ingested by chewing.

5. A chewable calcium carbonate-containing antacid tablet composition according to claim 4 comprising from about 0.04% to about 0.10% of 3-1-menthoxy propane 1,2-diol.

* * * * *